US008753864B2

(12) United States Patent
Aebi et al.

(10) Patent No.: US 8,753,864 B2
(45) Date of Patent: Jun. 17, 2014

(54) RECOMBINANT N-GLYCOSYLATED PROTEINS FROM PROCARYOTIC CELLS

(75) Inventors: Markus Aebi, Wettingen (CH); Michael Kowarik, Zürich (CH); Umesh Ahuja, Los Angeles, CA (US)

(73) Assignee: ETH Zurich, Zurich (CH)

( * ) Notice: Subject to any disclaimer, the term of this patent is extended or adjusted under 35 U.S.C. 154(b) by 1438 days.

(21) Appl. No.: 11/920,175

(22) PCT Filed: May 10, 2006

(86) PCT No.: PCT/EP2006/004397
§ 371 (c)(1),
(2), (4) Date: Oct. 21, 2009

(87) PCT Pub. No.: WO2006/119987
PCT Pub. Date: Nov. 16, 2006

(65) Prior Publication Data
US 2010/0062484 A1     Mar. 11, 2010

(30) Foreign Application Priority Data

May 11, 2005 (EP) .................................. 05010276

(51) Int. Cl.
*A61K 38/47* (2006.01)
*C12N 15/74* (2006.01)
*A61K 38/00* (2006.01)

(52) U.S. Cl.
USPC ................... 435/252.33; 435/252.8; 435/488; 435/200; 530/395; 514/2.8; 424/94.61

(58) Field of Classification Search
None
See application file for complete search history.

(56) References Cited

U.S. PATENT DOCUMENTS

| | | | |
|---|---|---|---|
| 5,643,758 | A | 7/1997 | Guan et al. |
| 2002/0019342 | A1 | 2/2002 | Bayer |
| 2004/0265954 | A1 | 12/2004 | Aebi et al. |
| 2005/0287628 | A1 | 12/2005 | Aebi et al. |

FOREIGN PATENT DOCUMENTS

| | | |
|---|---|---|
| CA | 1340184 | 12/1998 |
| CA | 2 360 205 A1 | 8/2000 |
| CA | 2 477 794 | 3/2003 |
| EP | 1 481 057 | 2/2006 |
| WO | WO-94/26906 | 11/1994 |
| WO | WO-00/52135 | 9/2000 |
| WO | WO-01/88117 | 11/2001 |
| WO | WO-02/00856 | 1/2002 |
| WO | WO-03/074687 | 9/2003 |
| WO | WO-2004-013151 A2 | 2/2004 |
| WO | WO 2004013151 A2 * | 2/2004 |

OTHER PUBLICATIONS

Wacker M. (2002) N-linked protein glycosylation: from eukaroytes to bacteria, A Dissertation submitted to Swiss Federal Institute of Technology Zurich, pp. 1-90.*
Prilipov et al. (1998) Identification and characterization of two quiescent porin genes, nmpC and ompN, in *Escherichia coli* BE, J. Bacteriol., vol. 180, No. 13, pp. 3398-3392.*
Raetz & Whitfield, Lipoplysaccharide Endotoxins, *NIH-PA Author Manuscript*, pp. 1-57, 19-25 (published in final edited form as: *Annual Rev. Biochem.*, 71:635-700 (2002) (Epub Nov. 9, 2001)).
Thibault et al., "Identification of the Carbohydrate Moieties and Glycosylation Motifs in *Campylobactor jejuni* Flagellin," The Journal of Biological Chemistry, vol. 276, No. 37, pp. 34862-34870 (Sep. 2001).
Guerry et al., "Identification and characterizatio of genes required for post-translational modification of *Campylobacter coli* VC167 flagellin," Molecular Microbiology, vol. 19, No. 2, pp. 369-378 (1996).
Doig et al., "Characterization of a post-translational modification of *Campylobacter* flagellin: identification of a sero-specific glycosyl moiety," Molecular Microbiology, Vo. 19, No. 2, pp. 379-387 (1996).
Whitfield et al., Structure, assembly and regulation of express of capsules iin *Escherichia coli*, Molecular Microbiology, vol. 31, No. 5, pp. 1307-1319 (1999).
Reeves et al., "Bacterial polysaccharide synthesis and gene nomenclature," Reviews, Elseview Science Ltd., pp. 495-503 (1996).
Ahmed, A. et al., "Safety and Immunogenicity of *Escherichia coli* O157 O-Specific Polysaccharide Conjugate Vaccine in 2-5—Year Old Children," Journal of Infectious Diseases, vol. 193, No. 4, pp. 515-521 (Feb. 15, 2006) (elec. pub. Jan. 13, 2006).
Anderson, P., "Antibody Responses to *Haemophilus influenzae* Type b and Diphtheria Toxin Induced by Conjugates of Oligosaccharides of the Type b Capsule with the Nontoxic Protein $CRM_{197}$," Infection and Immunity, vol. 39, No. 1, pp. 233-238 (Jan. 1983).
Baqar, S. et al., "Safety and immunogenicty of a prototype oral whole-cell killed *Campylobacter* vaccine administered with a mucosal adjuvant in non-human primates," Vaccine, vol. 13, No. 1, pp. 22-28 (Jan. 1995).
Braden et al., "Introduction to Protein Structure," Garland Publishing Inc., New York, pp. 247-268 (1991).
Burr, D.H. et al., "Prevention of disease in ferrets fed an inactivated whole cell *Campylobacter jejuni* vaccine," Vaccine, vol. 23, pp. 4315-4321 (Jul. 29, 2005) (available online May 3, 2005).
Butzler, J.P., "*Campylobacter*, from obscurity to celebrity," Clinical Microbiology and Infection, pp. 868-876 (Oct. 2004).
Casburn-Jones, A.C. et al., "Traveler's diarrhea," Journal of Gastroenterology and Hepatology, vol. 19, pp. 610-618 (Jun. 2004).
Chart, H. et al., "Serological identification of *Escherichia coli* O157:H7 infection in haemolytic uraemic syndrome," The Lancet, vol. 337, pp. 138-140 (Jan. 19, 1991).
Chemistry and Biology, vol. 39, No. 10, pp. 632-634 (2001).
Crushell, E. et al., "Enteric *Campylobacter*. Purging its Secrets?" Pediatric Research, vol. 55, No. 1, pp. 3-12 (Jan. 2004).
Fairweather, N.F. et al., "Cloning, Nucleotide Sequencing, and Expression of Tetanus Toxin Fragment C in *Escherichia coli*," Journal of Bacteriology, vol. 165, No. 1, pp. 21-27 (Jan. 1986).

(Continued)

Primary Examiner — Manjunath Rao
Assistant Examiner — Samuel Liu
(74) Attorney, Agent, or Firm — Jones Day (57) ABSTRACT

The present invention relates to recombinant N-glycosylated proteins, comprising one or more introduced N-glycosylated optimized amino acid sequence(s), nucleic acids encoding these proteins as well as corresponding vectors and host cells. In addition, the present invention is directed to the use of said proteins, nucleic acids, vectors and host cells for preparing medicaments. Furthermore, the present invention provides methods for producing said proteins.

7 Claims, 4 Drawing Sheets

(56) References Cited

OTHER PUBLICATIONS

Fass, R. et al., "Use of high density cultures of *Escherichia coli* for high level production of recombinant *Pseudomonas aeruginosa* exotoxin A," Applied Microbiolgy and Biotechnology, vol. 36, No. 1, pp. 65-69 (Oct. 1991).

Fattom A. et al., "Laboratory and Clinical Evaluation of Conjugate Vaccines Composed of *Staphylococcus aureus* Type 5 and Type 8 Capsular Polysaccharides Bound to *Pseudomonas aeruginosa* Recombinant Exoprotein A," Infection and Immunity, vol. 61, No. 3, pp. 1023-1032 (Mar. 1993).

Goebel, W.F. and Avery, O.T., "Chemo-Immunological Studies on Conjugated Carbohydrate-Proteins," Journal of Experimental Medicine, pp. 521-531 (1929).

Haberberger, R.L. et al., "Prospects and Problems of Development of a Vaccine against Diarrhea Caused by *Campylobacter*," Vaccine Research, vol. 3, pp. 15-22 (Nov. 1, 1994).

Karlyshev, A.V. et al., "The *Campylobacter jejuni* general glycosylation system is important for attachment to human epithelial cells and in the colonization of chicks," Microbiology, vol. 150, pp. 1957-1964 (Jun. 2004).

Konadu, E. et al., "Preparation, Characterization, and Immunological Properties in Mice of *Escherichia coli* O157 O-Specific Polysaccharide—Protein Conjugate Vaccines," Infection and Immunigy, vol. 62, No. 11, pp. 5048-5054 (Nov. 1994).

Konadu, E. et al., "Syntheses and Immunologic Properties of *Escherichia coli* O157 O-Specific Polysacharide and Shiga Toxin 1 B Subunit Conjugates in Mice," Infection and Immunity, vol. 67, No. 11, pp. 6191-6193 (Nov. 1999).

Konadu, E. et al., "Investigational Vaccine for *Escherichia coli* O157: Phase 1 Study of O157 O-Specific Polysaccharide-*Pseudomonas aeruginosa* Recombinant Exoprotein A Conjugates in Adults, Journal of Infectious Diseases," vol. 177, No. 2, pp. 383-387 (Feb. 1998).

Kowarik, M. et al., "N-Linked Glycosylation of Folded Proteins by the Bacterial Oligosaccharyltransferase," Science, vol. 314, pp. 1148-1150 (Nov. 17, 2006).

Lee, L.H. et al., "Evaluation of a Truncated Recombinanat Flagellin Subunit Vaccine against *Campylobacter jejuni*," Infection and Immunity, vol. 67, No. 11, pp. 5799-5805 (Nov. 1999).

Linton D. et al., "Functional analysis of the *Campylobacter jejuni* N-linked protein glycosylation pathway," Molecular Microbioloby, vol. 55, No. 6, pp. 1695-1703 (Mar. 2005).

Lukac, M. et al., "Toxoid of *Pseudomonas aeruginosa* Exotoxin A Generated by Deletion of an Active-Site Residue," Infection and Immunity, vol. 56, No. 12, pp. 3095-3098 (Dec. 1988).

Middlebrook, J.L. et al., "Bacterial Toxins: Cellular Mechanisms of Action," Microbiological Reviews, vol. 48, No. 3, pp. 199-221 (Sep. 1984).

Nairn, J.G., "Solutions, Emulsions, Suspensions and Extracts," Remington's Pharmaceutical Sciences, 18th ed., Mack Publishing Co., Chapter 83, pp. 1519-1544 (1990).

Panina-Bordignon, P. et al., "Universally immunogenic T cell epitopes: promiscuous binding to human MHC class II and promiscuous recognition by T cells*," European Journal of Immunology, vol. 29, pp. 2237-2242 (Dec. 1989).

Parkhill, J. et al., "The genome sequence of the food-borne pathogen *Campylobacter jejuni* reveals hypervariable sequences," Nature, vol. 403, pp. 665-668 (Feb. 10, 2000).

Passwell, J.H. et al., "Safety and Immunogenicity of Improved *Shegella* O-Specific Polysaccharide-Protein Conjugate Vaccines in Adults in Israel," Infection and Immunity, vol. 69, No. 3, pp. 1351-1357 (Mar. 2001).

Pearson, B.M. et al., "Comparative genome analysis of *Campylobacter jejuni* using whole genome DNA microarrays," FEBS Letter, vol. 554, FEBS 27782, pp. 224-230 (Nov. 6, 2003) (pub. online Oct. 16, 2003).

Pozsgay, V., "Synthesis of Glycoconjugate Vaccines again *Shigella dysenteriae* Type 1," Journal of Organic Chemistry, vol 63, pp. 5983-5999 (Aug. 21, 1998) (pub. on web Jul. 29, 1998).

Pozsgay, V. et al., "Protein conjugates of synthetic saccharides elicit higher levels of serum IgG lipopolysaccharide antibodies in mice than do those of the O-specific polysaccharide from *Shigella dysenteriae* type 1," Proceedings of the National Academy of Sciences, vol. 96, pp. 5194-5197 (Apr. 27, 1999).

Schaad, U.B. et al., "Safety and immunogenicity of *Pseudomonas aeruginosa* conjugate A vaccine in cystic fibrosis," The Lancet, vol. 338, pp. 1236-1237 (Nov. 16, 1991).

Schneerson, R. et al., Preparation, Characterization, and Immunogenicity of *Haemophilus influenzae* Type b Polysaccharide-Proteins Conjugates, Journal of Experimental Medicine, vol. 152, pp. 361-376 (Aug. 1, 1980).

Scott, D.A., "Vaccines against *Campylobacter jejuni*," Journal of Infectious Diseases, vol. 176, Suppl. 2, S183-S188 (Dec. 1997).

Szu, S.C. et al., "Laboratory and Preliminary Clinical Characterization of Vi Capsular Polysaccharide-Protein Conjugate Vaccines," Infection and Immunity, vol. 62, No. 10, pp. 4440-4444 (Oct. 1994).

Szymanski, C.M. et al., "Campylobacter Protein Glycosylation Affects Host Cell Interactions," Infection and Immunity, vol. 70, No. 4, pp. 2242-2244 (Apr. 2002).

Szymanski, C.M. et al. "Protein Glycosylation in Bacterial Mucosal Pathogens," Nature Reviews, Microbiology, vol. 3, pp. 225-237 (Mar. 2005 (pub. online Feb. 10, 2005).

Taylor, D.N. et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (*Plesiomonas shigelloides*) Bound to Bacterial Toxoids," Infection and Immunity, vol. 61, No. 9, pp. 3678-3687 (Sep. 1993).

Varki et al., "Essential of Glycobiology," Cold Spring Harbor Laboratory Press, Chapter 7, pp. 85-100 (1999).

Yao et al., "Isolation of motile and non-motile insertional mutants of *Campylobacter jejuni*: the role of motility in adherence and invasion of eukaryotic cells," Molecular Microbiology, vol. 14, No. 5, pp. 883-893, (Dec. 1994).

Alaimo, C. et al., "Two distinct but interchangeable mechanisms for flipping of lipid-linked oligosaccharides," EMBO Journal 25, pp. 967-976 (2006).

Altmann et al., "Insect cells as hosts for the expression of recombinant glycoproteins" Glycoconjugate Journal, 16, p. 109-23 (1993).

Baneyx, F., "Recombinant protein expression in *Escherichia coli*," Curr. Opin. Biotechnol. 10, pp. 411-421 (1999).

Berg, A. and de Kok, A., "2-Oxo Acid Dehydrogenase Multienzyme Complexes: The Central Role of the Lipoyl Domain," Bioliology Chemistry, 278, pp. 617-634 (1997).

Burda et al., "The dolichol pathway of N-linked glycosylation," Biochimica et Biophysica Acta, 1426, p. 239-57 (1999).

Bill, R.M. et al., "Expression and mutagenesis of recombinant human and murine erythropoietins in *Escherichia coli*," Biochimica et Biophysica Acta 1261, pp. 35-43 (1995).

Billman-Jacobe, H., "Expression in bacteria other than *Escherichia coli*," Curr. Opin. Biotechnol. 7, pp. 500-504 (1996).

Bugg, T.D. and Brandish, P.E., "From peptidoglycan to glycoproteins: Common features of lipid-linked oligosaccharide biosynthesis," FEMS Microbiol. Lett. 119, pp. 255-262 (1994).

Choi, J.H. and Lee, S.Y., "Secretory and extracellular production of recombinant proteins using *Escherichia coli*," Appl. Microbiol. Biotechnol. 64, pp. 625-635 (2004).

Crooks, Gavin E. et al., "WebLogo: A Sequence Logo Generator," Genome Research, vol. 14, No. 6, Jun. 2004, pp. 1188-1190, XP002408756, ISSN: 1088-9051.

Feldman et al., "Engineering N-linked protein glycosylation with diverse O antigen lipopolysaccharide structures in *Escherichia coli*," Proc. Natl. Acad. Sci. USA 102, pp. 3016-3021 (2005).

Francisco, J.A. et al., "Transport and anchoring of β-lactamase to the external surface of *Escherichia coli*," Proc. Natl. Acad. Sci. USA 89: 2713-2717 (1992).

Fry et al., "The lipopolysaccharide biosynthesis locus of *Campylobacter jejuni* 81116," Microbiology, vol. 144, p. 2049-61 (1998).

Fujita et al., "Synthesis of Neoglycoenzymes with Homogenous N-Linked Oligosaccharides Using Immobilized Endo-β-N-acetylglucosaminidase A," Biochemical and Biophysical Research Communications, 267, p. 134-38 (2000).

(56) References Cited

OTHER PUBLICATIONS

Gavel et al., "Sequence differences between glycosylated and non-glycosylated Asn-X-Thr/Ser acceptor sites: implications for protein engineering," Protein Eng, 3, p. 433-42 (1990).

Glover, K.J. et al., "Chemoenzymatic Synthesis of Glycopeptides with PglB, a Bacterial Oligosaccharyl Transferase from *Campylobacter jejuni*," Chemistry & Biology, vol. 12, pp. 1311-1316 (2005).

Grabenhorst et al., "Genetic engineering of recombinant glycoproteins and the glycosylation pathway in mammalian host cells," Glycoconjugate Journal, 16, p. 81-97 (1999).

Helenius, A. and Aebi, M., "Roles of N-linked Glycans in the Endoplasmic Reticulum," Annu. Rev. Biochem. 73, pp. 1019-1049 (2004).

Higgins et al., "Structure of the periplasmic component of a bacterial drug efflux pump," Proc. Natl. Acad. Sci. USA 101, pp. 9994-9999 (2004).

Hoiseth, S.K. and Stocker, B.A., "Aromatic-dependent *Salmonella typhimurium* are non-virulent and effective as live vaccines," Nature 291: 238-239 (1981).

Imperiali, B. and Shannon, K.L., "Differences between Asn-Xaa-Thr-containing peptides: a comparison of solution conformation and substrate behaviour with oligosaccharyl-transferase," Biochemistry 30, pp. 4374-4380 (1991).

Jeong, K.J. and Lee S.Y., "Secretory Production of Human Granulocyte Colony-Stimulating Factor in *Escherichia coli*," Protein Expression and Purification 23, pp. 311-318 (2001).

Johnson, J.M. and Church, G.M., "Alignment and Structure Prediction of Divergent Protein Families: Periplasmic and Outer Membrane Proteins of Bacterial Efflux Pumps," J. Mol. Biol. 287, pp. 695-715 (1999).

Kaniuk, N.A. et al. "Investigation of the Structural Requirements in the Lipopolysaccharide Core Acceptor for Ligation of O Antigens in the Genus *Salmonella*: WaaL 'Ligase' Is Not the Sole Determinant of Acceptor Specificity," J. Biological Chemistry 279: 36470-36480 (2004).

Kowarik, Michael et al., "Definition of the bacterial N-glycosylation site consensus sequence" EMBO (European Molecular Biology Organization) Journal, vol. 25, No. 9, May 2006, pp. 1957-1966, XP002408605, ISSN: 0261-4189.

Linton, D. et al., "Identification of N-acetylgalactosamine-containing glycoproteins PEB3 and CgpA in *Campylobacter jejuni*," Molecular Microbiology, Blackwell Scientific, Oxford, GB, vol. 42, No. 2, 2002, pp. 497-508, XP002267530.

Malissard et al., "The yeast expression system for recombinant glycosyltransferases," Glycoconjugate Journal, 16, p. 125-39 (1999).

Maras, et al., "Filamentous fungi as production organisms for glycoproteins of bio-medical interest," Glycoconjugate Journal, 16, p. 99-107 (1999).

Muller, A. et al., "An ATP-binding cassette-type cysteine transporter in *Campylobacter jejuni* inferred from the structure of an extracytoplasmic solute receptor protein," Mol. Microbiol. 57: 143-155 (2005).

Nita-Lazar, Mihai et al., "The N-X-S/T consensus sequence is required but not sufficient for bacterial N-linked protein glycosylation," Glycobiology, vol. 15, No. 4, Apr. 2005, pp. 361-367, XP002408606, ISSN: 0959-6658.

Paetzel, M. et al., "Signal Peptidases," Chem. Rev. 102: 4549-4580 (2002).

Petrescu et al., "Statistical analysis of the protein environment of *N*-glycosylation sites: implications for occupancy, structure, and folding," Glycobiology, vol. 14, No. 2, pp. 103-114, 2004.

Rudd, P.M. and Dwek, R.A., "Glycosylation: Heterogeneity and the 3D Structure of Proteins," Crit. Rev. Biochem. Mol. Biol. 32, pp. 1-100 (1997).

Schulz, H. et al., "Prototype of a Heme Chaperone Essential for Cytochrome c Maturation," Science 281 pp. 1197-1200 (1998).

Szymanski et al., "Evidence for a system of general protein glyscosylation in a *Campylobacter jejuni*," Molecular Microbiology, vol. 32, Issue 5, p. 1022-30 (Jun. 1999).

Simons, G. et al., "High-level expression of human interferon gamma in *Escherichia coli* under control of the $p_L$ promoter of bacteriophage lambda," Gene 28, pp. 55-64 (1984).

Valvano, M.A., "Export of O-Specific Lipopolysaccharide," Front. Biosci. 8, s452-471 (2003).

Wacker et al., "N-Linked Glycosylation in *Campylobacter jejuni* and its Functional Transfer into *E. coil*," Science, vol. 298, p. 1790-93 (Nov. 2002).

Wacker et al., "P.gIB, an oligosaccharyltransferase in the eubacterium *Campylobacter jejuni*?" Glycobiology, vol. 11, p. 871 (Oct. 2001).

Wacker, et al., "Substrate specificity of bacterial oligosaccharyltransferase suggest a common transfer mechanism for the bacterial and eukaryotic systems," Proc. Natl. Acad. Sci. 103, pp. 7088-7093 (2006).

Wernerus, H. and Stahl, S. "Biotechnological applications for surface-engineered bacteria," Biotechnol. Appl. Biochem. 40: 209-228 (2004).

Wyszynska, A. et al., "Oral immunization of chickens with avirulent *Salmonella* vaccine strain carrying *C. jejuni* 72Dz/92 cjaA gene elicits specific humoral immune response associated with protection against challenge with wild-type *Campylobacter*," Vaccine 22, pp. 1379-1389 (2004).

Young et al., "Structure of the N-Linked Glycan Present of Multiple Glycoproteins in the Gram-negative Bacterium, *Campylobacter jujuni*," The Journal of Biological Chemistry, vol. 277, No. 45, p. 42530-39 (Nov. 2002).

\* cited by examiner

RECOMBINANT N-GLYCOSYLATED PROTEINS FROM PROCARYOTIC CELLS

The present invention relates to recombinant N-glycosylated proteins, comprising one or more introduced N-glycosylated optimized amino acid consensus sequence(s), nucleic acids encoding these proteins as well as corresponding vectors and host cells. In addition, the present invention is directed to the use of said proteins, nucleic acids, vectors and host cells for preparing medicaments. Furthermore, the present invention provides methods for producing said proteins.

BACKGROUND OF THE INVENTION

N-linked protein glycosylation is an essential and conserved process occurring in the endoplasmic reticulum of eukarotic organisms. It is important for protein folding, oligomerization, stability, quality control, sorting and transport of secretory and membrane proteins (Helenius, A., and Aebi, M. (2004). Roles of N-linked glycans in the endoplasmic reticulum. Annu. Rev. Biochem. 73, 1019-1049).

Protein glycosylation has a profound influence on the antigenicity, the stability and the half-life of a protein. In addition, glycosylation can assist the purification of proteins by chromatography, e.g. affinity chromatography with lectin ligands bound to a solid phase interacting with glycosylated moieties of the protein. It is therefore established practice to produce many glycosylated proteins recombinantly in eukaryotic cells to provide biologically and pharmaceutically useful glycosylation patterns.

Only within recent years it was demonstrated that a bacterium, the food-borne pathogen *Campylobacter jejuni*, can also N-glycosylate its proteins (Szymanski, et al. (1999). Evidence for a system of general protein glycosylation in *Campylobacter jejuni*. Mol. Microbiol. 32, 1022-1030). The machinery required for glycosylation is encoded by 12 genes that are clustered in the so-called pgl locus. Disruption of N-gylcosylation affects invasion and pathogenesis of *C. jejuni* but is not lethal as in most eukaryotic organisms (Burda P. and M. Aebi, (1999). The dolichol pathway of N-linked glycosylation. Biochim Biophys Acta 1426(2):239-57). It is possible to reconstitute the N-glycosylation of *C. jejuni* proteins by recombinantly expressing the pgl locus and acceptor glycoprotein in *E. coli* at the same time (Wacker et al. (2002). N-linked glycosylation in *Campylobacter jejuni* and its functional transfer into *E. coli*. Science 298, 1790-1793).

European Patent Application No. 03 702 276.1 (European Patent 1 481 057), an earlier invention of the present inventors, teaches a procaryotic organism into which is introduced a nucleic acid encoding for (i) specific glycosyltransferases for the assembly of an oligosaccharide on a lipid carrier, (ii) a recombinant target protein comprising a consensus sequence "N-X-S/T", wherein X can be any amino acid except proline, and (iii) an oligosaccharyl transferase of *C. jejuni* (OTase) that covalently links said oligosaccharide to the consensus sequence of the target protein. Said procaryotic organism produces N-glycans with a specific structure which is defined by the type of the specific glycosyltransferases.

Even though the presence of the known N-glycosylation consensus sequence in a protein does allow for the N-glycosylation of recombinant target proteins in procaryotic organisms comprising the oligosaccharyl transferase (OTase) of *C. jejuni*, the N-glycosylation of some target proteins is often inefficient.

The object of the present invention is to provide proteins as well as means and methods for producing such proteins having an optimized efficiency for N-glycosylation that can be produced in procaryotic organisms in vivo. Another object of the present invention aims at the more efficient introduction of N-glycans into recombinant proteins for modifying antigenicity, stability, biological, prophylactic and/or therapeutic activity of said proteins. A further object is the provision of a host cell that efficiently displays recombinant N-glycosylated proteins of the present invention on its surface.

In a first aspect the present invention provides a recombinant N-glycosylated protein, comprising one or more of the following N-glycosylated optimized amino acid sequence(s):

D/E-X-N-Z-S/T, (optimized consensus sequence)

wherein X and Z may be any natural amino acid except Pro, and wherein at least one of said N-glycosylated partial amino acid sequence(s) is introduced.

It was surprisingly found that the introduction of specific partial amino acid sequence(s) (optimized consensus sequence(s)) into proteins leads to proteins that are efficiently N-glycosylated by the oligosaccharyl transferase (OST, OTase) from *Campylobacter* spp., preferably *C. jejuni*, in these introduced positions.

The term "partial amino acid sequence(s)" as it is used in the context of the present invention will also be referred to as "optimized consensus sequence(s)". The optimized consensus sequence is N-glycosylated by the oligosaccharyl transferase (OST,$_{[MW1]}$OTase) from *Campylobacter* spp., preferably *C. jejuni*, much more efficiently than the regular consensus sequence "N-X-S/T" known in the prior art.

In general, the term "recombinant N-glycosylated protein" refers to any heterologous poly- or oligopeptide produced in a host cell that does not naturally comprise the nucleic acid encoding said protein. In the context of the present invention this term refers to a protein produced recombinantly in any host cell, e.g. an eukaryotic or prokaryotic host cell, preferably a procaryotic host cell, e.g. *Escherichia* ssp., *Campylobacter* ssp., *Salmonella* ssp., *Shigella* ssp., *Helicobacter* ssp., *Pseudomonas* ssp., *Bacillus* ssp., more preferably *Escherichia coli*, *Campylobacter jejuni*, *Salmonella typhimurium* etc., wherein the nucleic acid encoding said protein has been introduced into said host cell and wherein the encoded protein is N-glycosylated by the OTase from *Campylobacter* spp., preferably *C. jejuni*, said transferase enzyme naturally occurring in or being introduced recombinantly into said host cell.

In accordance with the internationally accepted one letter code for amino acids the abbreviations D, E, N, S and T denote aspartic acid, glutamic acid, asparagine, serine, and threonine, respectively. Proteins according to the invention differ from natural or prior art proteins in that one or more of the optimized consensus sequence(s) D/E-X-N-Z-S/T is/are introduced and N-glycosylated. Hence, the proteins of the present invention differ from the naturally occurring *C. jejuni* proteins which also contain the optimized consensus sequence but do not comprise any additional (introduced) optimized consensus sequences.

The introduction of the optimized consensus sequence can be accomplished by the addition, deletion and/or substitution of one or more amino acids. The addition, deletion and/or substitution of one or more amino acids for the purpose of introducing the optimized consensus sequence can be accomplished by chemical synthetic strategies well known to those skilled in the art such as solid phase-assisted chemical peptide synthesis. Alternatively, and preferred for larger polypeptides, the proteins of the present invention can be prepared by standard recombinant techniques.

The proteins of the present invention have the advantage that they may be produced with high efficiency and in any procaryotic host comprising a functional pgl operon from *Campylobacter* spp., preferably *C. jejuni*. Preferred alternative OTases from *Campylobacter* spp. for practicing the aspects and embodiments of the present invention are *Campylobacter coli* and *Campylobacter lari* (see Szymanski, C. M. and Wren, B. W. (2005). Protein glycosylation in bacterial mucosal pathogens. Nat. Rev. Microbiol. 3: 225-237). The functional pgl operon may be present naturally when said procaryotic host is *Campylobacter* spp., preferably *C. jejuni*. However, as demonstrated before in the art and mentioned above, the pgl operon can be transferred into cells and remain functional in said new cellular environment.

The term "functional pgl operon from *Campylobacter* spp., preferably *C. jejuni*" is meant to refer to the cluster of nucleic acids encoding the functional oligosaccharyl transferase (OTase) of *Campylobacter* spp., preferably *C. jejuni*, and one or more specific glycosyltransferases capable of assembling an oligosaccharide on a lipid carrier, and wherein said oligosaccharide can be transferred from the lipid carrier to the target protein having one or more optimized amino acid sequence(s): D/E-X N-Z-S/T by the OTase. It to be understood that the term "functional pgl operon from *Campylobacter* spp., preferably *C. jejuni*" in the context of this invention does not necessarily refer to an operon as a singular transcriptional unit. The term merely requires the presence of the functional components for N-glycosylation of the recombinant protein in one host cell. These components may be transcribed as one or more separate mRNAs and may be regulated together or separately. For example, the term also encompasses functional components positioned in genomic DNA and plasmid(s) in one host cell. For the purpose of efficiency, it is preferred that all components of the functional pgl operon are regulated and expressed simultaneously.

It is important to realize that only the functional oligosaccharyl transferase (OTase) should originate from *Campylobacter* spp., preferably *C. jejuni*, and that the one or more specific glycosyltransferases capable of assembling an oligosaccharide on a lipid carrier may originate from the host cell or be introduced recombinantly into said host cell, the only functional limitation being that the oligosaccharide assembled by said glycosyltransferases can be transferred from the lipid carrier to the target protein having one or more optimized consensus sequences by the OTase. Hence, the selection of the host cell comprising specific glycosyltransferases naturally and/or incapacitating specific glycosyltransferases naturally present in said host as well as the introduction of heterologous specific glycosyltransferases will enable those skilled in the art to vary the N-glycans bound to the optimized N-glycosylation consensus site in the proteins of the present invention.

As a result of the above, the present invention provides for the individual design of N-glycan-patterns on the proteins of the present invention. The proteins can therefore be individualized in their N-glycan pattern to suit biological, pharmaceutical and purification needs.

In a preferred embodiment, the proteins of the present invention may comprise one but also more than one, preferably at least two, preferably at least 3, more preferably at least 5 of said N-glycosylated optimized amino acid, sequences.

The presence of one or more N-glycosylated optimized amino acid sequence(s) in the proteins of the present invention can be of advantage for increasing their antigenicity, increasing their stability, affecting their biological activity, prolonging their biological half-life and/or simplifying their purification.

The optimized consensus sequence may include any amino acid except proline in position(s) X and Z. The term "any amino acids" is meant to encompass common and rare natural amino acids as well as synthetic amino acid derivatives and analogs that will still allow the optimized consensus sequence to be N-glycosylated by the OTase. Naturally occurring common and rare amino acids are preferred for X and Z. X and Z may be the same or different.

It is noted that X and Z may differ for each optimized consensus sequence in a protein according to the present invention.

The N-glycan bound to the optimized consensus sequence will be determined by the specific glycosyltransferases and their interaction when assembling the oligosaccharide on a lipid carrier for transfer by the OTase. Those skilled in the art can design the N-glycan by varying the type(s) and amount of the specific glycosyltransferases present in the desired host cell.

N-glycans are defined herein as mono-, oligo- or polysaccharides of variable compositions that are linked to an $\epsilon$-amide nitrogen of an asparagine residue in a protein via an N-glycosidic linkage. Preferably, the N-glycans transferred by the OTase are assembled on an undecaprenol-pyrophosphate lipid-anchor that is present in the cytoplasmic membrane of gram-negative or positive bacteria. They are involved in the synthesis of O antigen, O polysaccharide and peptidoglycan (Bugg, T. D., and Brandish, P. E. (1994). From peptidoglycan to glycoproteins: common features of lipid-linked oligosaccharide biosynthesis. FEMS Microbiol Lett 119, 255-262; Valvano, M. A. (2003). Export of O-specific lipopolysaccharide. Front Biosci 8, s452-471).

In a preferred embodiment, the recombinant protein of the present invention comprises one or more N-glycans selected from the group of N-glycans from *Campylobacter* spp., preferably *C. jejuni*, the N-glycans derived from oligo- and polysaccharides transferred to O antigen forming O polysaccharide in Gram-negative bacteria or capsular polysaccharides from Gram-positive bacteria, preferably: *P. aeruginosa* O9, O11; *E. coli* O7, O9, O16, O157 and *Shigella dysenteriae* O1 and engineered variants thereof obtained by inserting or deleting glycosyltransferases and epimerases affecting the polysaccharide structure.

In a further preferred embodiment the recombinant protein of the present invention comprises two or more different N-glycans.

For example, different N-glycans on the same protein can prepared by controlling the timing of the expression of specific glycosyltransferases using early or late promoters or introducing factors for starting, silencing, enhancing and/or reducing the promoter activity of individual specific glycosyltransferases. Suitable promoters and factors governing their activity are available to those in the art routinely and will not be discussed further.

There is no limitation on the origin of the recombinant protein of the invention. Preferably said protein is derived from mammalian, bacterial, viral, fungal or plant proteins. More preferably, the protein is derived from mammalian, most preferably human proteins. For preparing antigenic recombinant proteins according to the invention, preferably for use as active components in vaccines, it is preferred that the recombinant protein is derived from a bacterial, viral or fungal protein.

In a further preferred embodiment the present invention provides for recombinant proteins wherein either the protein and/or the N-glycan(s) is (are) therapeutically and/or prophylactically active. The introduction of at least one optimized and N-glycosylated consensus sequence can modify or even introduce therapeutic and/or prophylactic activity in a protein. In a more preferred embodiment it is the protein and/or the N-glycan(s) that is (are) immunogenically active. In this case the introduced N-glycosylation(s) may have a modifying effect on the proteins biological activity and/or introduce new antigenic sites and/or may mask the protein to evade degrading steps and/or increase the half-life.

The recombinant proteins of the present invention can be efficiently targeted to the outer membrane and/or surface of host cells, preferably bacteria, more preferably gram-negative bacteria. For assisting the surface display and/or outer membrane localisation it is preferred that the recombinant protein of the invention further comprises at least one polypeptide sequence capable of targeting said recombinant protein to the outer membrane and/or cell surface of a bacterium, preferably a gram-negative bacterium.

In a preferred embodiment the recombinant protein of the invention is one, wherein said targeting polypeptide sequence is selected from the group consisting of type II signal peptides (Paetzel, M., Karla, A., Strynadka, N. C., and Dalbey, R. E. 2002. Signal peptidases. Chem Rev 102: 4549-4580.) or outer membrane proteins (reviewed in Wernerus, H., and Stahl, S. 2004. Biotechnological applications for surface-engineered bacteria. Biotechnol Appl Biochem 40: 209-228.[mk2]), preferably selected from the group consisting of the full length protein or the signal peptides of OmpH1 from *C. jejuni*, JlpA from *C. jejuni*, outer membrane proteins from *E. coli*, preferably OmpS, OmpC, OmpA, OprF, PhoE, Lam B, Lpp'OmpA (a fusion protein for surface display technology, see Francisco, J. A., Earhart, C. F., and Georgiou, G. 1992. Transport and anchoring of beta-lactamase to the external surface of *Escherichia coli*. Proc Natl Aced Sci USA 89: 2713-2717.), and the Inp protein from *Pseudomonas aeruginosa*.

In a different aspect, the present invention relates to a nucleic acid encoding a recombinant protein according to the invention. Preferably, said nucleic acid is a mRNA, a DNA or a PNA, more preferably a mRNA or a DNA, most preferably a DNA. The nucleic acid may comprise the sequence coding for said protein and, in addition, other sequences such as regulatory sequences, e.g. promoters, enhancers, stop codons, start codons and genes required to regulate the expression of the recombinant protein via the mentioned regulatory sequences, etc. The term "nucleic acid encoding a recombinant protein according to the invention" is directed to a nucleic acid comprising said coding sequence and optionally any further nucleic acid sequences regardless of the sequence information as long as the nucleic acid is capable of producing the recombinant protein of the invention in a host cell containing a functional pgl operon from *Campylobacter* spp., preferably *C. jejuni*. More preferably, the present invention provides isolated and purified nucleic acids operably linked to a promoter, preferably linked to a promoter selected from the group consisting of known inducible and constitutive prokaryotic promoters, more preferably the tetracycline promoter, the arabinose promoter, the salicylate promoter, lac-, trc-, and tac promotors (Baneyx, F. (1999). Recombinant protein expression in *Escherichia coli*. Curr Opin Biotechnol 10, 411-421; Billman-Jacobe, H. (1996). Expression in bacteria other than *Escherichia coli*. Curr Opin Biotechnol 7, 500-504.). Said operably linked nucleic acids can be used for, e.g. vaccination.

Furthermore, another aspect of the present invention relates to a host cell comprising a nucleic acid and/or a vector according to the present invention. The type of host cell is not limiting as long as it accommodates a functional pgl operon from *C. jejuni* and one or more nucleic acids coding for recombinant target protein(s) of the present invention. Preferred host cells are prokaryotic host cells, more preferably bacteria, most preferably those selected from the group consisting of *Escherichia* ssp., *Campylobacter* ssp., *Salmonella* ssp., *Shigella* ssp., *Helicobacter* ssp., *Pseudomonas* ssp., *Bacillus* ssp., preferably *Escherichia coli*, more preferably *E. coli* strains Top10, W3110, CLM24, BL21, SCM6 and SCM7 (Feldman et al., (2005). Engineering N-linked protein glycosylation with diverse O antigen lipopolysaccharide structures in *Escherichia coli*. Proc. Natl. Acad. Sci. USA 102, 3016-3021; Alaimo, C., Catrein, I., Morf, L., Marolda, C. L., Callewaert, N., Valvano, M. A., Feldman, M. F., Aebi, M. (2006). Two distinct but interchangeable mechanisms for flipping of lipid-linked oligosaccharides. EMBO Journal 25, 967-976) and *S. enterica* strains SL3261 (*Salmonella enterica* sv. *Typhimurium* LT2 (delta) aroA, see Hoiseth, S. K., and Stocker, B. A. 1981, Aromatic-dependent *Salmonella typhimurium* are non-virulent and effective as live vaccines. Nature 291:238-239), SL3749 (*Salmonella enterica* sv. *Typhimurium* LT2 waaL, see Kaniuk et al., J. Biol. Chem. 279: 36470-36480) and SL3261ΔwaaL.

In a more preferred embodiment the host cell according to the invention is one that is useful for the targeting to the outer membrane and/or surface display of recombinant proteins according to the invention, preferably one, wherein said host cell is a recombinant gram-negative bacterium having:

i) a genotype comprising nucleotide sequences encoding for
   a) at least one natural or recombinant specific glycosyltransferase for the assembly of an oligosaccharide on a lipid carrier,
   b) at least one natural or recombinant prokaryotic oligosaccharyl transferase (OTase) from *Campylobacter* spp., preferably *C. jejuni*,
   c) at least one recombinant protein according to the invention, preferably a protein further comprising a targeting polypeptide, and ii) a phenotype comprising a recombinant N-glycosylated protein according to the invention that is located in and/or on the outer membrane of the gram-negative bacterium.

The host cell for the above embodiment is preferably selected from the group consisting of *Escherichia* ssp., *Campylobacter* ssp., *Shigella* ssp, *Helicobacter* ssp. and *Pseudomonas* ssp., *Salmonella* ssp., preferably *E. coli*, more preferably *E. coli* strains Top10, W3110, CLM24, BL21, SCM6 and SCM7, and *S. enterica* strains SL3261, SL3749 and SL3261ΔwaaL. (see Hoiseth, S. K., and Stocker, B. A. 1981. Aromatic-dependent *Salmonella typhimurium* are non-virulent and effective as live vaccines. Nature 291: 238-239), SL3749 (Kaniuk, N. A., Vinogradov, E., and Whitfield, C. 2004. Investigation of the structural requirements in the lipopolysaccharide core acceptor for ligation of O antigens in the genus *Salmonella*: WaaL "ligase" is not the sole determinant of acceptor specificity. J Biol Chem 279: 36470-36480).[mk4]

Because preferred proteins of the present invention may have a therapeutic or prophylactic activity by themselves and/or due to the introduced N-glycosylation sites, they can be used for the preparation of a medicament. The type of protein for practicing the invention is not limited and, therefore, proteins of the invention such. as EPO, IFN-alpha, TNFalpha, IgG, IgM, IgA, interleukins, cytokines, viral and bacterial proteins for vaccination like *C. jejuni* proteins such as HisJ (Cj0734c), AcrA (Cj0367c), OmpH1 (Cj0982c), Diphteria toxin (CRM197), Cholera toxin, *P. aeruginosa* exoprotein, to name just a few, and having introduced therein the optimized N-glycosylated consensus sequence are useful for preparing a medicament (Wyszynska, A., Raczko, A., L is, M., and Jagusztyn-Krynicka, E. K. (2004). Oral immunization of chickens with avirulent *Salmonella* vaccine strain carrying *C. jejuni* 72Dz/92 cjaA gene elicits specific humoral immune response associated with protection against challenge with wild-type *Campylobacter*. Vaccine 22, 1379-1389).

In addition, the nucleic acids and/or vectors according to the invention are also useful for the preparation of a medicament, preferably for use in gene therapy.

Moreover, a host cell according to the invention, preferably one that has a phenotype comprising an N-glycosylated recombinant protein of the invention that is located in and/or on the outer membrane of a bacterium, preferably a gram-negative bacterium, more preferably one of the above-listed gram-negative bacteria, is particularly useful for the preparation of a medicament.

More preferably, a protein of the invention is used for the preparation of a medicament for the therapeutic and/or prophylactic vaccination of a subject in need thereof.

In a more preferred embodiment the present invention relates to the use of a nucleic acid and/or a vector according to the invention for the preparation of a medicament for the therapeutic and/or prophylactic vaccination of a subject in need thereof, preferably by gene therapy.

The host cells of the invention displaying said N-glycosylated recombinant proteins are particularly useful for preparing vaccines, because the displayed N-glycosylated proteins are abundantly present on the host cell's surface and well accessible by immune cells, in particular their hydrophilic N-glycans, and because the host cells have the added effect of an adjuvant, that, if alive, may even replicate to some extent and amplify its vaccination effects.

Preferably, the host cell for practicing the medical aspects of this invention is an attenuated or killed host cell.

Another advantage of the use of the inventive host cells for preparing medicaments, preferably vaccines, is that they induce IgA antibodies due to the cellular component.

Preferably, said host cells are used according to the invention for inducing IgA antibodies in an animal, preferably a mammal, a rodent, ovine, equine, canine, bovine or a human.

It is preferred that said subject in need of vaccination is avian, mammalian or fish, preferably mammalian, more preferably a mammal selected from the group consisting of cattle, sheep, equines, dogs, cats, and humans, most preferably humans. Fowls are also preferred.

A further aspect of the present invention relates to a pharmaceutical composition, comprising at least one protein, at least one nucleic acid, a least one vector and/or at least one host cell according to the invention. The preparation of medicaments comprising proteins or host cells, preferably attenuated or killed host cells, and the preparation of medicaments comprising nucleic acids and/or vectors for gene therapy are well known in the art. The preparation scheme for the final pharmaceutical composition and the mode and details of its administration will depend on the protein, the host cell, the nucleic acid and/or the vector employed.

In a preferred embodiment, the pharmaceutical composition of the invention comprises a pharmaceutically acceptable excipient, diluent and/or adjuvant.

The present invention provides for a pharmaceutical composition comprising at least one of the following, (i) a recombinant protein, a host cell, a nucleic acid and/or a recombinant vector being/encoding/expressing a recombinant protein according to the present invention, and (ii) a pharmaceutically acceptable excipient, diluent and/or adjuvant.

Suitable excipients, diluents and/or adjuvants are well-known in the art. An excipient or diluent may be a solid, semi-solid or liquid material which may serve as a vehicle or medium for the active ingredient. One of ordinary skill in the art in the field of preparing compositions can readily select the proper form and mode of administration depending upon the particular characteristics of the product selected, the disease or condition to be treated, the stage of the disease or condition, and other relevant circumstances (*Remington's Pharmaceutical Sciences*, Mack Publishing Co. (1990)). The proportion and nature of the pharmaceutically acceptable diluent or excipient are determined by the solubility and chemical properties of the pharmaceutically active compound selected, the chosen route of administration, and standard pharmaceutical practice. The pharmaceutical preparation may be adapted for oral, parenteral or topical use and may be administered to the patient in the form of tablets, capsules, suppositories, solution, suspensions, or the like. The pharmaceutically active compounds of the present invention, while effective themselves, can be formulated and administered in the form of their pharmaceutically acceptable salts, such as acid addition salts or base addition salts, for purposes of stability, convenience of crystallization, increased solubility, and the like.

A further aspect of the present invention is directed to a method for producing N-linked glycosylated proteins, comprising the steps of:

a) providing a recombinant organism, preferably a prokaryotic organism, comprising nucleic acids coding for
   i) a functional pgl operon from *Campylobacter* spp., preferably *C. jejuni*, and
   ii) at least one recombinant target protein comprising one or more of the following N-glycosylated optimized amino acid consensus sequence(s):

D/E-X-N-Z-S/T, wherein X and Z may be any natural amino acid except Pro, and wherein at least one of said N-glycosylated optimized amino acid consensus sequence(s) is introduced, and b) culturing the recombinant organism in a manner suitable for the production and N-glycosylation of the target protein(s).

Preferably, the target protein is one of the above described recombinant proteins according to the invention.

In a preferred method of the invention, the functional pgl operon from *Campylobacter* spp., preferably *C. jejuni*, comprises nucleic acids coding for
   i) recombinant OTase from *Campylobacter* spp., preferably *C. jejuni*, and
   ii) recombinant and/or natural specific glycosyltransferases from *Campylobacter* spp., preferably *C. jejuni*, and/or
   iii) recombinant and/or natural specific glycosyltransferases from species other than *Campylobacter* spp.,
for the assembly of an oligosaccharide on a lipid carrier to be transferred to the target protein by the OTase.

Moreover, in a preferred embodiment the present invention relates to a method for preparing a host cell according to the invention comprising the steps of:
i) providing a gram-negative bacterium,
ii) introducing into said bacterium at least one nucleotide sequence encoding for
   a) at least one recombinant specific glycosyltransferase for the assembly of an oligosaccharide on a lipid carrier, and/or
   b) at least one recombinant oligosaccharyl transferase (OTase) from *Campylobacter* spp., preferably *C. jejuni*, and/or c) at least one recombinant protein comprising one or more of the following N-glycosylated optimized amino acid consensus sequence(s):

D/E-X-N-Z-S/T, wherein X and Z may be any natural amino acid except Pro, and wherein at least one of said N-glycosylated optimized amino acid consensus sequence(s) is introduced, and iii) culturing said bacterium until at least one recombinant N-glycosylated protein coded by the nucleotide sequence of c) is located in and/or on the outer membrane of the gram-negative bacterium.

For practicing the preferred methods above, the recombinant procaryotic organism or host cell is preferably selected from the group of bacteria consisting of *Escherichia* ssp., *Campylobacter* ssp., *Salmonella* ssp., *Shigella* ssp., *Helicobacter* ssp., *Pseudomonas* ssp., *Bacillus* ssp., preferably *Escherichia coli*, preferably *E. coli* strains Top10, W3110, CLM24, BL21, SCM6 and SCM7, and *S. enterica* strains SL3261, SL3749 and SL3261ΔwaaL.

Exemplary methods for removing the outer membrane of a cell, preferably a prokaryotic cell, more preferably a gram-negative bacterial cell, are suitable enzymatic treatment methods, osmotic shock detergent solubilisation and the French press method.

Most preferred, the present invention relates to a method, wherein recombinant or natural specific glycosyltransferases from species other than *Campylobacter* spp., preferably *C. jejuni*, are selected from the group of glycosyltransferases and epimerases originating from bacteria, archea, and/or eukaryota that can be functionally expressed in said host cell.

FIGURES

FIG. 1 illustrates the N-glycosylation of Lip proteins derived from constructs A to C (see example 1). *E. coli* Top 10 cells carrying a functional pgl operon from *C. jejuni* (Wacker et al., 2002, supra) and a plasmid coding for constructs A (lane 2), B (lane 1), and C (lane 3) or a mutant of construct C with the mutation D121A (lane 4). Proteins were expressed and purified from periplasmic extracts. Shown is the SDS-PAGE and Coomassie brilliant blue staining of the purified protein fractions.

FIG. 3 shows the engineering of multiple glycosylation sites in OmpH1. The ΔwaaL strain SCM6 was co-transformed with plasmid pACYCpgl (encoding entire pgl locus) and plasmids expressing wild type OmpH1 (lane 1), OmpH1$^{N139S}$-myc (lane 2), OmpH1$^{KGN \to NIT, HFGDD \to DSNIT}$-myc (lane 3), OmpH1$^{RGD \to NIT, HFGDD \to DSNIT}$-myc (lane 4), OmpH1$^{KGN \to NIT, RGD \to NIT}$-myc (lane 5), OmpH1$^{KGN \to NIT, RGD \to NIT, HFGDD \to DSNIT}$-myc (lane 6) or OmpH1$^{RGD \to NIT, V83T}$-myc (lane 7). The cells were grown aerobically, induced with 0.5% arabinose for 3 hours prior to analysis. Whole cell lysates were TCA precipitated after equalizing the optical density of the cultures as described in the materials and methods section. The proteins were separated by 15% SDS-PAGE and transferred onto a PVDF membrane. First panel, immunoblot of whole cell lysates probed with anti-myc tag antibodies. Bottom panel, immunoblot of whole cell lysates probed with glycan-specific antiserum. The positions of unglycosylated- and glycosylated OmpH1 are indicated on the right.

FIG. 4. Fluorescence microscopy of cells expressing various OmpH1 variants. Cultures of *E. coli* strains CLM24 or SCM6 containing the expression plasmid for the wild type OmpH1 and its variants were equalized to $OD_{600}$ of 0.25/ml. Cells were washed two times with phosphate-buffered saline (PBS), pH 7.4 and 100 µl cell suspensions was dropped onto gelatinized glass slides and incubated at room temperature (RT) for 30 min inside a humidified chamber. All subsequent steps in the whole-cell immunofluorescence labeling were done at room temperature inside a humidified chamber. The unbound cells were removed and rest was fixed with 4% paraformaldehyde containing PBS for 30 min at RT. Importantly, paraformaldehyde is considered not to permeabilize cells but keeping the compartimentalization by membranes intact. Fixed cells were washed two times with PBS and resuspended blocking buffer containing 5% BSA in PBS. After blocking, the cells were incubated with anti-myc monoclonal mouse IgG (1:50, Calbiochem) and/or anti-glycan antiserum (1:4000) for 1 h in 100 µl of PBS containing 5% BSA. The cells were washed three times with 100 µl of PBS for 5 min each and incubated with secondary anti-rabbit antibody conjugated to FITC (1:250, Jackson Immunoresearch Laboratories) and/or anti-mouse antibody conjugated to Cy3 (1:250, Jackson Immunoresearch Laboratories) for 1 h in 100 µl of PBS containing 5% BSA. If required, 4,6-diamino-2-phenylindole (DAPI) (Sigma) (0.5 µg/ml) was added at the time of secondary antibody incubation to stain for bacterial DNA. The secondary antibody was rinsed from the cells PBS, and coverslips were mounted on slides by using vectashield (Vector Laboratories) mounting medium and sealed with nail polish. Fluorescence microscopy was performed by the using an Axioplan2 microscope (Carl Zeiss). Images were combined by using Adobe Photoshop, version CS2. SCM6 cells expressing OmpH1 (panel A), OmpH1$^{N139S}$ (panel B), OmpH1$^{C20S}$ (panel C), OmpH1$^{KGN \to NIT, HFGDD \to DSNIT}$ (panel D), OmpH1$^{RGD \to NIT, HFGDD \to DSNIT}$ (panel E), OmpH1$^{KGN \to NIT, RGD \to NIT}$ (panel F), OmpH1$^{V83T, KGN \to NIT}$ (panel G), and OmpH1$^{KGN \to NIT, RGD \to NIT, HFGDD \to DSNIT}$ (panel H). The first column is a merge of the pictures in columns 2, 3, and 4 represented in greytones on black background. Column 2: blue fluorescence in greytones from DAPI stain, column 3: green fluorescence from glycan specific fluorescence, column 4: red fluorescence from anti-myc staining.

The following examples serve to illustrate further the present invention and are not intended to limits its scope in any way.

EXAMPLES

Selection of AcrA as Model Protein for Optimizing N-glycosylation

To optimize the acceptor protein requirements for N-glycosylation detailed studies were performed on the *C. jejuni* glycoprotein AcrA (Cj0367c). AcrA is a periplasmic lipoprotein of 350 amino acid residues. It has been shown that secretion to the periplasm but not lipid-anchoring is a prerequisite for glycosylation (Nita-Lazar et al., 2005, supra). The signal for export can either be the native AcrA signal sequence or the heterologous PelB signal when expressed in *E. coli*. Of the five potential N-linked glycosylation sequons (N117, N123, N147, N273, N274) the same two ones are used in *C. jejuni* and *E. coli* (N123 and N273 (Nita-Lazar et al., 2005, supra)). AcrA was chosen as model because it is the only periplasmic N-glycoprotein of *C. jejuni* for which detailed structural information is available. Recently, the crystal structure of an AcrA homologue, the MexA protein from the Gram-negative bacterium *P. aeruginosa*, was published (Higgins et al., (2004). Structure of the periplasmic component of a bacterial drug efflux pump. Proc. Natl. Acad. Sci. USA 101, 9994-9999). Both proteins are members of the so-called periplasmic efflux pump proteins (PEP,(Johnson, J. M. and Church, G. M. (1999). Alignment and structure prediction of divergent protein families: periplasmic and outer membrane proteins of bacterial efflux pumps. J. Mol. Biol. 287, 695-715)). The elongated molecule contains three linearly arranged subdomains: an α-helical, anti-parallel coiled-coil which is held together at the base by a lipoyl domain, which is followed by a six-stranded β-barrel domain. The 23-28 residues at the N-terminus and 95-101 residues in the C-terminus are unstructured in the crystals. MexA and AcrA protein sequences are 29.3% identical and 50% similar. Thus, the two proteins likely exhibit a similar overall fold.

Example 1

Elucidation of the Primary Peptide Sequence that Timers Glycosylation

It is known that lipoyl domains similar to MexA of *P. aeruginosa* and accordingly also in AcrA of *C. jejuni* form a compact protein that can be individually expressed in *E. coli* (reviewed by Berg, A, and de Kok, A. (1997). 2-Oxo acid dehydrogenase multienzyme complexes. The central role of the lipoyl domain. Biol. Chem. 378, 617-634). To check which acceptor peptide sequence was required for N-glycosylation by the pgl machinery in *E. coli* the lipoyl domain of AcrA was taken. It was used as a molecular scaffold to transport peptides of different lengths to the periplasm and present them to the pgl machinery in vivo.

Therefore, a plasmid coding for the lipoyl domain (Lip) was constructed and N-terminally fused to the signal sequence of OmpA (Choi, J. H., and Lee, S. Y. (2004). Secretory and extracellular production of recombinant proteins using *Escherichia coli*. Appl Microbiol Biotechnol 64, 625-635) and C-terminally to a hexa histag. Cloning was performed to place the gene expression under the control of the arabinose promoter. For the Lip domain borders amino acid positions were chosen that appeared at the same positions as the domain borders of the Lipoyl domain part in MexA. To test different peptides for their ability to accept an N-glycan stretches of the sequence were inserted between the two hammerhead-like parts of the Lip domain. The stretches consisted of sequences comprising the N-glycosylation site N123 of *C. jejuni* AcrA. The resulting open reading frames consisted of the sequences coding for the OmpA signal sequence, the N-terminal hammerhead-like part of AcrA (D60-D95, the numbering of the amino acids refers to the mature AcrA polypeptide sequence numbering), the different stretches containing the native N123 glycosylation site of AcrA (see below), the C-terminal hammerhead-like part of AcrA-Lip (L167-D210) and the C-terminal his-tag.

Construction of the plasmids was achieved by standard molecular biology techniques. Three stretches containing the native N123 glycosylation site of AcrA of different lengths were inserted between the two halves of Lip resulting in three different ORFs:

Construct A contains A118-S130 resulting in a protein sequence of:

(sequence 1)
<u>MKKTAIAIAVALAGFATVAQA</u>DVIIKPQVSGVIVNKLFKAGDKVKKGQTL

FIIEQD<u>Q</u>ASKDFNRSKALFSQLDHTEIKAPFDGTIGDALVNIGDYVSAST

TELVRVTNLNPIYADG*SHHHHHH*.

Construct B contains F122-E138 resulting in a protein sequence of:

(sequence 2)
<u>MKKTAIAIAVALAGFATVAQA</u>DVIIKPQVSGVIVNKLFKAGDKVKKGQTL

FIEEQD<u>Q</u>FNRSKALFSQSAISQKELDHTEIKAPFDGTIGDALVNIDGYVS

ASTTELVRVTNLNPIYADG*SHHHHHH*.

Construct C contains D121-A127 resulting in a protein sequence of:

(sequence 3)
<u>MKKTAIAIAVALAGFATVAQA</u>DVIIKPQVSGVIVNKLFKAGDKVKKGQTL

FIIEQD<u>Q</u>DFNRSKALDHTEIKAPFDGTIGDALVNIGDYVSASTTELVRVT

NLNPIYADG*SHHHHHH*.

The underlined stretches of sequence indicate the OmpA signal peptide, singly underlined residues were introduced for cloning reasons or to render the protein resistant to degradation. Bold: glycosylation site corresponding to N123 of AcrA. Italics: hexa-histag. The corresponding genes were expressed under the control of the arabinose promoter in the backbone of the plasmid pEC415 (Schulz, H., Hennecke, H., and Thony-Meyer, L. (1998). Prototype of a heme chaperone essential for cytochrome c maturation. Science 281, 1197-1200).

Figure 1:
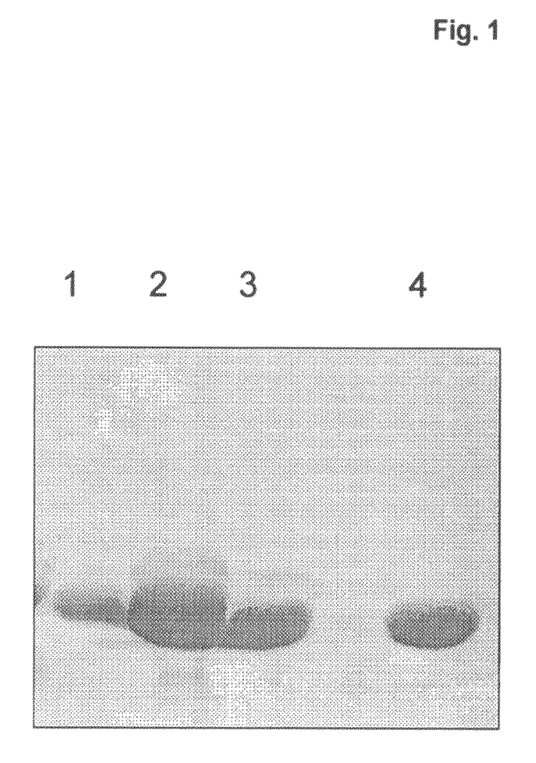

To check which of the three stretches triggered glycosylation of the Lip proteins protein expression experiments were performed. *E. coli* Top10 cells (Invitrogen, Carlsbad, Calif., USA) carrying pACYCpgl or pACYCpglmut (Wacker et al., 2002, supra) and a plasmid coding constructs A, B or C were grown in LB medium containing ampicillin and chloramphenicol up to an OD of 0.5 at 37° C. For induction 1/1000 volume 20% arabinose (w/v) solution was added and the cells were grown for another 2 hrs. The cells were then harvested by centrifugation and resuspended in 20 mM Tris/HCl, pH 8.5, 20% sucrose (w/v), 1 mM EDTA, 1 mM PMSF, and 1 g/l (w/v) lysozyme and incubated at 4° C. for 1 hr. Periplasmic extracts were obtained after pelletting of the spheroblasts and diluted with 1/9 volume (v/v) of 10× buffer A (3 M NaCl, 0.5 M Tris/HCl, pH 8.0 and 0.1 M imidazole) and MgSO$_4$ added to 2.5 mM. Ni-affinity purification was performed on 1 ml Ni-Sepharose columns from Amersham Pharmacia Biotech (Uppsala, Sweden) in buffer A. Proteins were eluted in buffer A containing 0.25 M imidazole.

FIG. 1 shows Coomassie brilliant blue stained SDS-PAGE gel of the peak elution fractions from the Ni-purified periplasmic extracts. The expression analysis showed that construct B produced a prominent single protein species (FIG. 1, lane 1). Constructs A and C both lead, in addition to the prominent protein, to a second protein band with slower electrophoretic mobility (FIG. 1, lanes 2 and 3). That the heavier protein species was indeed glycosylated was proven by MALDI-TOF/TOF (not shown). The only amino acid missing in construct B but present in A and C was D121, the aspartate residue 2 positions N-terminally to the glycosylated N123. This demonstrates that D121 plays an important role for glycosylation by the OTase. To verify that D121 is essential for glycosylation it was mutated to alanine in construct C. Expression analysis resulted in only one protein band (FIG. 1, lane 4), thus showing that D121 is important for glycosylation. Furthermore, the fact that an artificial peptide display protein can be glycosylated shows that a short peptide of the D/E-X-N-Y-S/T type contains all information for *C. jejuni*-borne N-glycosylation to occur.

Example 2

Verification of Example 1; AcrA-D121A is not Glycosylated at N123

To confirm the findings from the peptide display approach an aspartate to alanine mutation was inserted at position 121 (D121A, i.e. 2 residues before the glycosylated N123) in the full length soluble version of the AcrA protein and it was tested whether the site N123 could still be glycosylated in *E. coli*. In order to test this AcrA-D121A was expressed and its glycosylation status was analyzed. For the analysis an engineered AcrA was used. It differed from the original *C. jejuni* gene in that it contains the PelB signal sequence (Choi and Lee, 2004, supra) for secretion into the periplasm and a C-terminal hexa histag for purification. It has been shown that this AcrA variant gets secreted, signal peptide-cleaved and glycosylated as the lipid anchored, native protein (Nita-Lazar et al., 2005, supra). The following is the protein sequence of the soluble AcrA protein:

(SEQ ID NO: 4)
<u>MKYLLPTAAAGLLLLAAQPAMA</u>MHMSKEEAPKIQMPPQPVTTMSAKSEDL

PLSFTYPAKLVSDYDVIIKPQVSGVIVNKLFKAGDKVKKGQTLFIIEQDK

FKASVDSAYGQALMAKATFENASKDFNRSKALFSKSAISQKEYDSSLATF

NNSKASLASARAQLANARIDLDHTEIKAPFDGTIGDALVNIGDYVSASTT

ELVRVTNLNPIYADFFISDTDKLNLVRNTQSGKWDLDSIHANLNLNGETV

QGKLYFIDSVIDANSGTVKAKAVFDNNNSTLLPGAFATITSEGFIQKNGF

KVPQIGVKQDQNDVYVLLVKNGKVEKSSVHISYQNNEYAIIDKGLQNGDK

IILDNFKKIQVGSEVKEIGAQLE*HHHHHH*

The underlined residues are the PelB signal peptide, italics the hexa-histag, and bold the two natural glycosylation sites at N123 and N273. A plasmid containing the ORF for the above protein in the pEC415 plasmid (Schulz et al., 1998) was constructed to produce pAcrAper.

Figure 2:
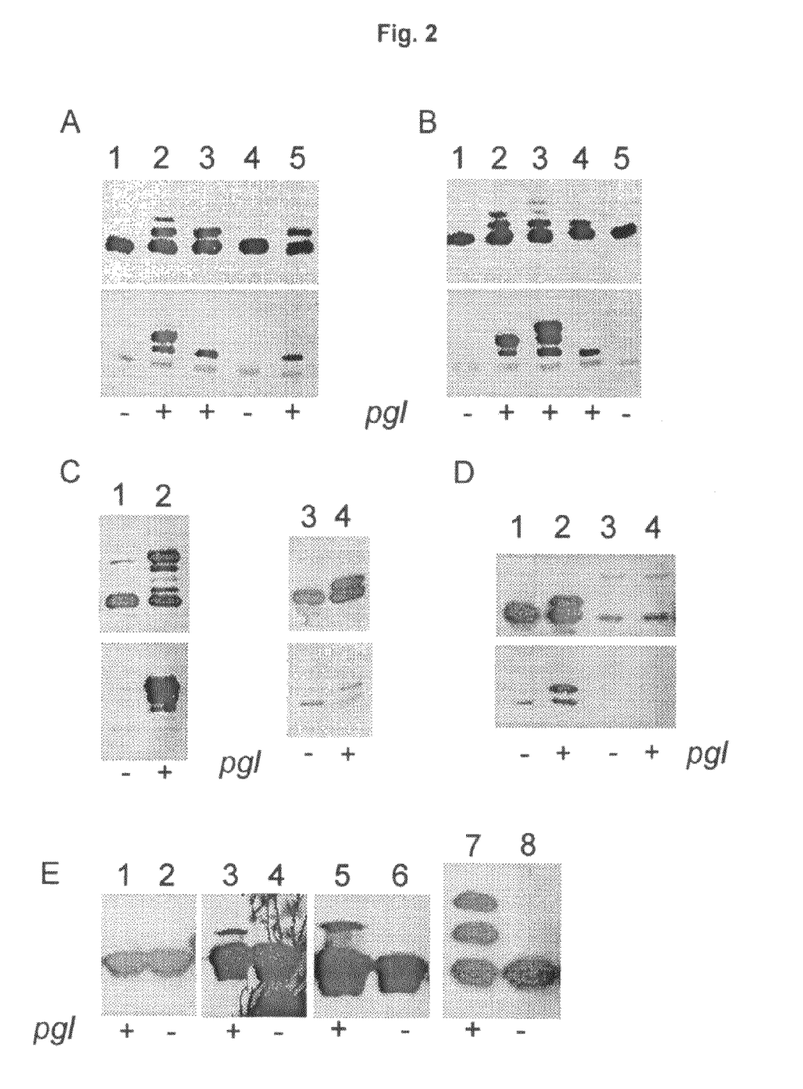
FIG. 2 shows the N-glycosylation analysis of the different proteins that were analyzed for the sequence specific N-glycosylation by the *C. jejuni* pgl operon (Wacker et al., 2002, supra) in CLM24 cells (Feldman et al., (2005). Engineering N-linked protein glycosylation with diverse 0 antigen lipopolysaccharide structures in *Escherichia coli*. Proc. Natl. Acad. Sci. USA 102, 3016-3021) or Top10 cells (panel E lanes 1-6) or SCM7 cells (Alaimo, C., Catrein, I., Morf, L., Marolda, C. L., Callewaert, N., Valvano, M. A., Feldman, M. F., Aebi, M. (2006). Two distinct but interchangeable mechanisms for flipping of lipid-linked oligosaccharides. EMBO Journal 25, 967-976) (panel E, lanes 7, 8) expressing said proteins from a plasmid. Shown are SDS-PAGE separated periplasmic extracts that were transfered to Nitrocellulose membrane and visualized with specific antisera. In panels A-D the top panel show immunoblots probed with anti AcrA antiserum (Wacker et al. 2002, supra; Nita-Lazar, M., Wacker, M., Schegg, B., Amber, S., and Aebi, M. (2005). The N-X-S/T consensus sequence is required but not sufficient for bacterial N-linked protein glycosylation. Glycobiology 15, 361-367), whereas the bottom panels show immunoblots probed with R12 antiserum (Wacker et al., 2002, supra). + and − indicate the presence of the functional or mutant pgl operon in the cells. Panel A contains samples of the soluble wildtype AcrA with the pelB signal sequence and the hexa histag (lanes 1, 2), AcrA-N273Q (lane 3, 4), and AcrA-D121A (lane 5). Panel B: AcrA (lanes 1, 2), AcrA-T145D (lane 3), AcrA-N123Q-N273Q-T145D (lanes 4, 5). Panel C: AcrA-F115D-T145D (lanes 1, 2), AcrA-N123Q-N273Q-N272D (lanes 3, 4). Panel D: AcrA-N273Q (lanes 1, 2), AcrA-N273Q-F122P (lanes 3, 4). Panel E: CtxB (lanes 1, 2), CtxB-W88D (lanes 3, 4), CtxB-Q56/DSNIT (lanes 5, 6), and CtxB-W88D-Q56/DSNIT.

The assay to test the glycosylation status of AcrA and mutants thereof (see below) was as follows: expression of AcrA was induced with 0.02% arabinose in exponentially growing *E. coli* CLM24 (Feldman et al., 2005, supra) cells containing the plasmid-borne pgl operon in its active or inactive form (pACYCpgl or pACYCpglmut, see (Wacker et al., 2002; supra)) and a plasmid coding for AcrA (pAcrAper). After four hours of induction, periplasmic extracts were prepared as described above and analyzed by SDS-PAGE, electrotransfer and immunodetection with either anti-AcrA antiserum or R12 antiserum. The latter is specific for *C. jejuni* N-glycan containing proteins (Wacker et al., 2002, supra).

The first two lanes of FIG. 2A show AcrA in the absence and presence of a functional pgl operon. Only one band appears in the absence but three in the presence of the functional pgl operon (FIG. 2A, top panel). These correspond to unglycosylated AcrA (lane 1) and un-, mono- and diglycosylated AcrA (lane 2). That the two heavier proteins in lane 2 were glycosylated was confirmed by the R12 western blot (lane 2, bottom panel). When the mutant AcrA-N273Q was expressed the same way, only the monoglycosylated AcrA was detected in presence of the functional glycosylation pgl operon (lane 3). Unglycosylated AcrA was detected in absence of the functional pgl locus (lane 4). Analysis of the mutant AcrA-D121A produced only two bands, one of them glycosylated (lane 5) as observed with AcrA-N273Q in lane 3. This means that D121 is essential for efficient glycosylation at position 123-125.

Example 3

Introducing Artificial Glycosylation Sites into AcrA

To test if the introduction of an aspartate residue could generate a glycosylation site, AcrA mutants were generated in which the residue in the −2 position of the not used glycosylation sites in positions N117 and N147 of soluble AcrA were exchanged for aspartate (F115D, T145D). It was then tested whether the modified glycosylation sites could be glycosylated by the same assay as described in example 2. Both mutations were individually inserted either into the wildtype sequence of the soluble version of AcrA or in the double mutant in which both used glycosylation sites were deleted (N123Q and N273Q). Periplasmic extracts of cultures induced for 4 hrs were prepared, separated by SDS page and analyzed by Western blotting (FIG. 2B). As controls the samples of wildtype glycosylated and non glycosylated AcrA were run on the same gel (lanes 1 and 2). The T145D mutation affected the −2 position of the natively not used glycosylation sequon N147-S149. Upon expression of AcrA-T145D Western blotting with anti AcrA antiserum resulted in four bands, the highest of them with slower electrophoretic mobility than the doubly glycosylated protein in lane 2 (lane 3 in FIG. 2B). The R12 blot confirmed that the fourth band was a triply glycosylated AcrA. Despite the low intensity towards anti AcrA the heaviest band gave the strongest signal with the glycosylation specific R12 antiserum. When the same mutant AcrA-T145D was expressed in the absence of the native N-glycosylation sequence (AcrA-N123Q-N273Q-T145D), only monoglycosylated AcrA was detected in the presence of a functional pgl operon (FIG. 2B, lane 4), that was missing in absence of a functional pgl operon (lane 5). This demonstrates that the heavier band in lane 4 was glycosylated.

Hence, by simply introducing the T145D mutation an optimized glycosylation site was generated (DFNNS).

To further confirm that it is possible to introduce a glycosylation site by inserting an aspartate residue in the −2 position, the natively not used sites N117-S119 and N274-T276 were changed to optimize N-glycosylation. For this purpose further mutants were generated (FIG. 2C). Expression of AcrA-F115D-T145D in the above described system resulted in five protein species detected with the anti AcrA antiserum (lane 2). This is indicative for four glycosylations taking place on the same AcrA molecule. When the detection was performed with the C. jejuni N-glycan-specific R12 antiserum, a ladder of five bands was detected. The lowest faint band is unglycosylated AcrA because it is also present in the absence of glycosylation (lane 1), the highest results in a strong signal probably due to the five antigenic determinants in a fourfold glycosylated AcrA. Thus, the two introduced sites (at N117 and N147) and the two natively used sites (N123 and N273) are used and glycosylated by the pgl machinery. Expression of AcrA-N123Q-N273Q-N272D with and without the pgl operon demonstrated that a third artificially introduced glycosylation site, N274 (DNNST), was also recognized by the pgl operon (FIG. 2C, lanes 3 and 4).

The above experiments confirm the finding that the bacterial N-glycosylation site recognized by the OTase of C. jejuni consists partly of the same consensus as the eukaryotic one (N-X-S/T, with X≠P) but, in addition, an aspartate in the −2 position is required for increasing efficiency. Furthermore, they demonstrate that it is possible to glycosylate a protein at a desired site by recombinantly introducing such an optimized consensus sequence.

Example 4

Verification of Position −1 in the Optimized N-glycosylation Sequence

A further experiment was performed to test whether the −1 position in the bacterial glycosylation site exhibits the same restrictions as the +1 position in eukaryotes (Imperiali, B., and Shannon, K. L. (1991). Differences between Asn-Xaa-Thr-containing peptides: a comparison of solution conformation and substrate behaviour with oligosaccharyl-transferase. Biochemistry 30, 4374-4380; Rudd, P. M., and Dwek, R. A. (1997). Glycosylation: heterogeneity and the 3D structure of proteins. Crit. Rev. Biochem. Mol. Biol. 32, 1-100). A proline residue at +1 is thought to restrict the peptide in such a way that glycosylation is inhibited. To test if a similar effect could also be observed in the −1 position a proline residue was introduced at that position of the first natively used site in a point mutant that had the second native site knocked out (AcrA-N273Q-F122P). The control expression of AcrA-N273Q showed a monoglycosylated protein in the presence of a functional pgl operon (FIG. 2D, lane 1 and 2). However, AcrA-N273Q-F122P was not glycosylated (FIG. 2D, lanes 3 and 4). This indicates that proline inhibited bacterial N-glycosylation when it constitutes the residue between the asparagine and the negatively charged residue of the −2 position.

Sequence alignments of all the sites known to be glycosylated by the C. jejuni pgl machinery indicate that they all comprise a D or E in the −2 position (Nita-Lazar et al., 2005, supra; Wacker et al., 2002, supra; Young et al., (2002). Structure of the N-linked glycan present on multiple glycoproteins in the Gram-negative bacterium, Campylobacter jejuni. J. Biol. Chem. 277, 42530-42539). Thus, it was established that the glycosylation consensus sequence for bacteria can be optimized by a negatively charged amino acid in the −2 position, resulting in D/E-X-N-Z-S/T, wherein X & Z≠P.

Example 5

N-Glycosylation of a Non-C. jejuni Protein

To demonstrate that the primary sequence requirement (optimized consensus sequence) is sufficient for N-glycosylation in bacteria, it was tested whether a non-C. jejuni protein could be glycosylated by applying the above strategy. Cholera toxin B subunit (CtxB) was employed as a glycosylation target. The corresponding gene was amplified from Vibrio cholerae in such a way that it contained the coding sequence of the OmpA signal sequence on the N-terminus and a hexa-histag at the C-terminus, just the same as constructs A through C in example 1. The resulting DNA was cloned to replace construct A in the plasmids employed in example 1. A point mutation of W88 to D or a D insertion after W88 generated an optimized glycosylation site (DNNKT). The wildtype and W88D CtxB proteins containing the signal sequence and his-tag were expressed in E. coli Top 10 and other cell types in the presence and absence of the functional pgl locus from C. jejuni. When periplasmic extracts from Top10 cells were analyzed by SDS-PAGE, electrotransfer and consecutive immunoblotting with a CtxB antiserum, only CtxB W88D produced a higher and thus glycosylated band in the pgl locus background (FIG. 2E, compare lanes 3 and 4). A consensus sequence (DSNIT) was also inserted by replacing G54 or Q56 of CtxB (the latter is denoted CtxB-Q56/DSNIT), i.e. in one of the loops that was reported to contribute to the ganglioside GM1 binding activity of CtxB. Lanes 5 and 6 of FIG. 2E demonstrate that the engineered protein (exemplified by the construct which contains the peptide sequence DSNIT instead of Q56 expressed in Top10 cells) produced a lower mobility and thus glycosylated band in glycosylation competent but not glycosylation-deficient cells when analyzed in the same way as described above. It was also demonstrated that a CtxB containing two manipulations, i.e. the insertion of D after W88 as well as DSNIT replacing Q56, was double-glycosylated in SCM7 cells (Alaimo et al., EMBO Journal 25: 967-976 (2006)) (panel E, lanes 7 and 8). The double-glycosylated protein CtxB shown in lane 7 was $Ni^{2+}$ affinity-purified and analyzed by ESI-MS/MS after in-gel trypsinization according to standard protocols. The expected glycopeptides were detected confirming that bacterial N-glycosylation can also be directed to a non-C. jejuni protein by mutating or inserting the optimized consensus sequence according to the invention for bacterial N-glycosylation (not shown). Examples of other suitable exemplary E. coli strains for practicing the present invention are W3110, CLM24, BL21 (Stratagene, La Jolla, Calif., USA), SCM6 and SCM7.

The amino acid sequence of the CtxB protein used here is indicated below (recombinant OmpA signal sequence underlined, hexa-histag italics, W88 bold):

(SEQ ID NO: 5)
MKKTAIAIAVALAGFATVAQATPQNITDLCAEYHNTQIHTLNDKIFSYTE

SLAGKREMAIITFKNGATFQVEVPGSQHIDSQKKAIERMKDTLRIAYLTE

AKVEKLCVWNNKTPHAIAAISMANG*SHHHHHH*

Example 6

Introduction of Artificial N-glycosylation Sites into the *C. jejuni* Outer Membrane Protein, OmpH1

Figure 3:
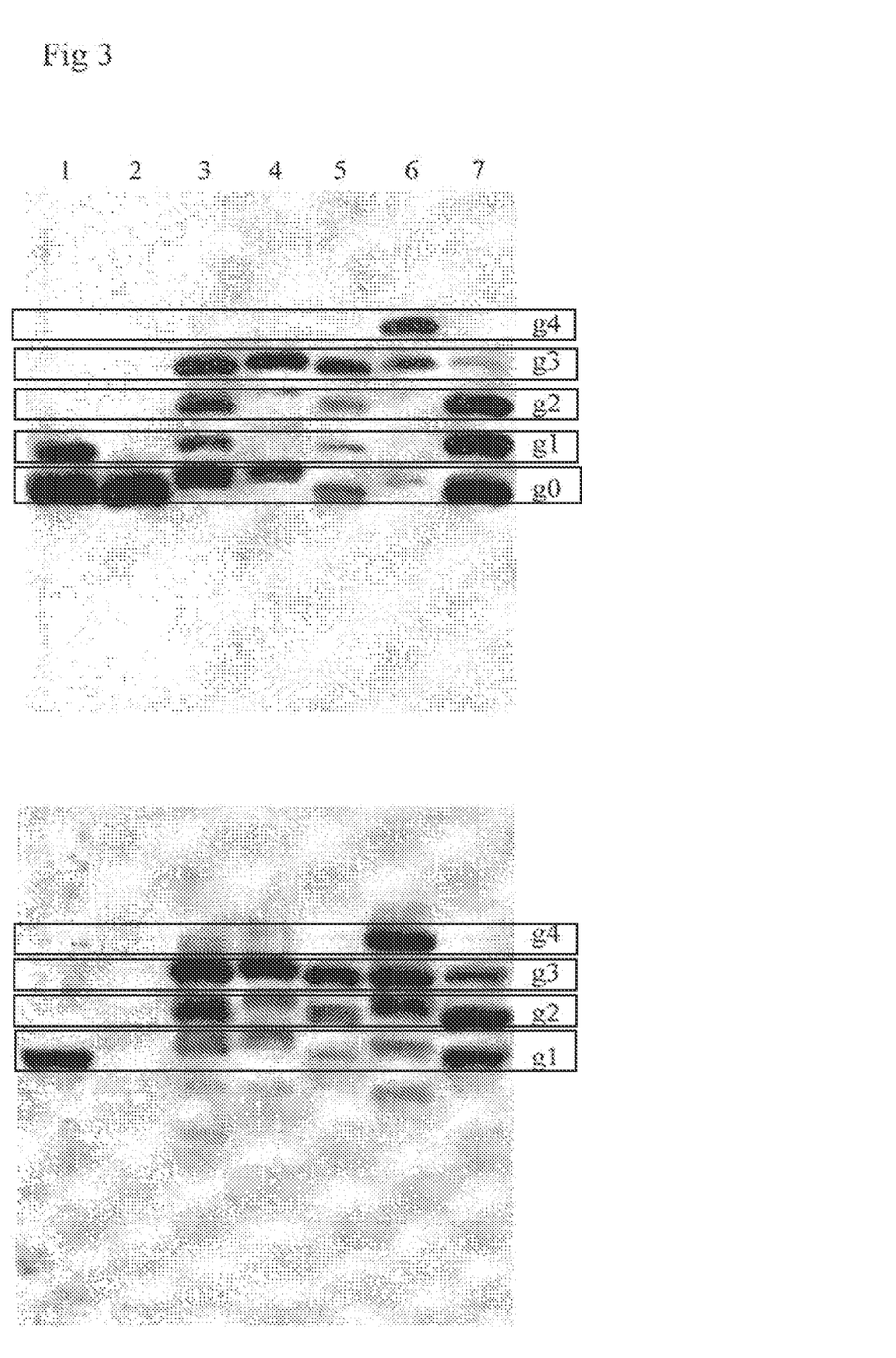

A potential application of the N-glycosylation in bacteria is the display of the glycan on the surface of a bacterial host cell in order to link the pheno- to the genotype and thereby select for specific genetic mutations. To demonstrate that N-glycans can be presented on outer membrane proteins the OmpH1 protein was engineered in a way that it contained multiple optimized consensus sites according to the invention. The sites were engineered into loop regions of the protein as deduced from the known crystal structure (Muller, A., Thomas, G. H., Horler, R., Brannigan, J. A., Blagova, E., Levdikov, V. M., Fogg, M. J., Wilson, K. S., and Wilkinson, A. J. 2005. An ATP-binding cassette-type cysteine transporter in *Campylobacter jejuni* inferred from the structure of an extracytoplasmic solute receptor protein. Mol. Microbiol. 57: 143-155). Previous experiments showed that the best glycosylation sequons were generated by the mutations V83T, K59N-G60I-N61T, R190N-G191I-D192T and H263D-F264S-G265N-D266I-D267T. For surface display it was desired to evaluate different combinations of those introduced sites in order to establish the most N-glycan-specific sample. The combinations were generated in a wild type OmpH1 encoding plasmid construct and tested in a similar manner as described for AcrA. FIG. 3 shows the analysis of various OmpH1 variants harboring multiple glycosylation sequons in addition to the existing wild type sequon. OmpH1 variants were generated with three (lane 3, 4, 5 and 7) and four glycosylation sequons (lane 6). A wild type OmpH1 with only one glycosylation sequon and a mutant lacking the critical asparagine for glycosylation were also included in the experiment. All variants tested here did not only demonstrate a high level of glycosylation efficiency but also that every glycosylation sequon was utilized. The results were confirmed with *Campylobacter* N-glycan specific immuneserum (FIG. 3 lower panel).

The following is the protein sequence of the OmpH1 protein of *Campylobacter jejuni* (strain 81-176) with attached myc tag in italics:

(SEQ ID NO: 5)

MKKILLSVLTTFVAVVLAACGGNSDSKTLNSLDKIKQNGVVRIGVFGDKP

PFGYVDEKGNNQGYDIALAKRIAKELFGDENKVQFVLVEAANRVEFLKSN

KVDIILANFTQTPERAEQVDFCLPYMKVALGVAVPKDSNITSVEDLKDKT

LLLNKGTTADAYFTQDYPNIKTLKYDQNTETFAALMDKRGDALSHDNTLL

FAWVKDHPDFKMGIKELGNKDVIAPAVKKGDKELKEFIDNLIIKLGQEQF

FHKAYDETLKAHFGDDVKADDVVIEGGKIL*EQKLISEEDL*

The native glycosylation site in the protein is bold, the signal sequence underlined.

Example 7

Figure 4:
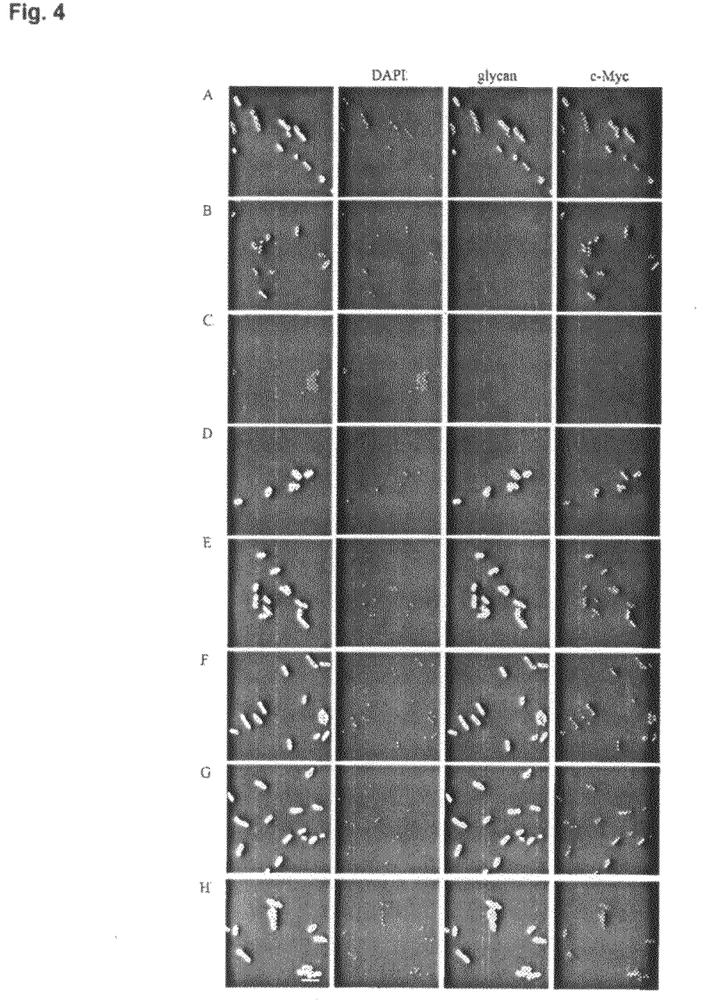

Surface Display of N-glycans from *C. jejuni* on OmpH1 on the Outer Membrane of *E. coli* Cells In order to answer the question whether multiple glycosylated OmpH1 variants can be displayed on the surface of bacterial cells, immunofluorescence was performed on bacterial CLM24 or SCM6 (which is SCM7 ΔwaaL) cells expressing various OmpH1 variants. A wild type OmpH1 and a mutant lacking the critical asparagine for glycosylation were included in the experiment. In addition, a C20S mutant was constructed in order to retain the protein in the periplasm, thus serving as a control in the experiment. Immunostaining was carried out on the cells treated with paraformaldehyde. Paraformaldehyde fixes cells without destroying the cell structure or compartmentalization. The c-Myc- and N-glycan-specific immune serum in combination with corresponding secondary antibodies conjugated to FITC and Cy3 were used to detect the protein (red fluorescence) and N-glycan (green) on the bacterial cell surface, respectively. Additionally, 4,6-diamino-2-phenylindole (DAPI, blue) was employed to stain for bacterial DNA to unambiguously differentiate between bacterial cells and cellular debris. When the cells expressing wild type OmpH1 were stained, immunofluorescence specific to the protein as well as the N-glycan was detected (FIG. 4, panel A). When a mutant lacking the critical asparagine N139S was stained with both anti-Myc- and N-glycan-specific immune serum only the protein but not glycan specific signals were obtained (panel 4 B) indicating specificity of the N-glycan-specific immune serum. When the protein was retained within the periplasm as in the C20S mutant, no protein specific, red immunofluorescence was detected indicating that the antibodies were unable to diffuse within the cell and were competent enough to detect any surface phenomenon (panel 4 C). Next, cells expressing multiple OmpH1 variants different in glycosylation were stained: OmpH1$^{KGN \to NIT, HFGDD \to DSNIT}$ (panel 4 D), OmpH1$^{RGD \to NIT, HFGDD \to DSNIT}$ (panel 4 E), OmpH1$^{KGN \to NIT, RGD \to NIT}$ (panel 4 F) OmpH1$^{V83T, KGN \to NIT}$ (panel 4 G) and OmpH1 $^{KGN \to NIT, RGD \to NIT, HFGDD \to DSNIT}$ (panel 4H). All the OmpH1 variants were double-stained indicating the presence of glycosylated protein on the bacterial surface. FIG. 4 is represented in grayscale, the first column is a merge picture of the other pictures of the same row. Panels of FIG. 4 are indicated as letters A-H and include the four pictures presented to the right of each of letters A-H.

The invention claimed is:

1. A recombinantly produced first organism, which is an E.coli. cell, into which is introduced nucleic acids encoding:
   a) a glycosyltransferase derived from a second organism which is a bacterial cell, wherein said glycosyltransferase assembling an oligosaccharide on a lipid carrier,
   b) a recombinant target protein derived from a third organism which is a bacterium, wherein the target protein comprises one or more inserted N-glycosylation optimized amino acid consensus sequence D/E-X-N-Z-S/T, wherein X and Z are independently selected from any natural amino acid except Pro, and wherein a nucleic acid sequence encoding said consensus sequence(s) is inserted through genetic engineering into the nucleic acid encoding said target protein in order to achieve an increased or optimized efficiency of the N-glycosylation of said target protein in the E.coli. cell compared to the same protein which does not comprise said N-glycosylation optimized amino acid consensus sequence; and
   c) an oligosaccharyl transferase which is derived from a fourth organism which is a bacterium;
   wherein said consensus sequence is N-glycosylated with said oligosaccharide by said oligosaccharyl transferase, wherein said second, third, and fourth organisms are different organisms.

2. The first organism of claim 1, comprising at least two, at least three, or at least five recombinant target proteins.

3. The first organism of claim 1, wherein the nucleic acids encoding said recombinant target protein further encode at least one polypeptide sequence capable of targeting said recombinant target protein to the outer membrane of the E.coli. cell.

4. The first organism of claim 3, wherein said polypeptide sequence comprises a type II signal peptide sequence or an outer membrane protein sequence from a Gram-negative bacterium.

5. The first organism of claim 1, wherein said first organism comprises a waaL gene deletion.

6. The first organism of claim 1, wherein said first organism E.coli. is different from the species of said second organism.

7. The first organism of claim 1, wherein said insertion through genetic engineering comprises insertion of a point mutation in said target protein.

* * * * *

SEQUENCE LISTING

<160> NUMBER OF SEQ ID NOS: 6

<210> SEQ ID NO 1
<211> LENGTH: 123

<212> TYPE: PRT
<213> ORGANISM: Artificial
<220> FEATURE:
<223> OTHER INFORMATION: Lip with N123 glycosylation site of AcrA and
      hexa His tag

<400> SEQUENCE: 1

```
Met Lys Lys Thr Ala Ile Ala Ile Ala Val Ala Leu Ala Gly Phe Ala
1               5                   10                  15

Thr Val Ala Gln Ala Asp Val Ile Ile Lys Pro Gln Val Ser Gly Val
            20                  25                  30

Ile Val Asn Lys Leu Phe Lys Ala Gly Asp Lys Val Lys Lys Gly Gln
        35                  40                  45

Thr Leu Phe Ile Ile Glu Gln Asp Gln Ala Ser Lys Asp Phe Asn Arg
    50                  55                  60

Ser Lys Ala Leu Phe Ser Gln Leu Asp His Thr Glu Ile Lys Ala Pro
65                  70                  75                  80

Phe Asp Gly Thr Ile Gly Asp Ala Leu Val Asn Ile Gly Asp Tyr Val
                85                  90                  95

Ser Ala Ser Thr Thr Glu Leu Val Arg Val Thr Asn Leu Asn Pro Ile
            100                 105                 110

Tyr Ala Asp Gly Ser His His His His His His
        115                 120
```

<210> SEQ ID NO 2
<211> LENGTH: 126
<212> TYPE: PRT
<213> ORGANISM: Artificial
<220> FEATURE:
<223> OTHER INFORMATION: Lip with N123 glycosylation site of AcrA and
      hexa His tag

<400> SEQUENCE: 2

```
Met Lys Lys Thr Ala Ile Ala Ile Ala Val Ala Leu Ala Gly Phe Ala
1               5                   10                  15

Thr Val Ala Gln Ala Asp Val Ile Ile Lys Pro Gln Val Ser Gly Val
            20                  25                  30

Ile Val Asn Lys Leu Phe Lys Ala Gly Asp Lys Val Lys Lys Gly Gln
        35                  40                  45

Thr Leu Phe Ile Ile Glu Gln Asp Gln Phe Asn Arg Ser Lys Ala Leu
    50                  55                  60

Phe Ser Gln Ser Ala Ile Ser Gln Lys Glu Leu Asp His Thr Glu Ile
65                  70                  75                  80

Lys Ala Pro Phe Asp Gly Thr Ile Gly Asp Ala Leu Val Asn Ile Gly
                85                  90                  95

Asp Tyr Val Ser Ala Ser Thr Thr Glu Leu Val Arg Val Thr Asn Leu
            100                 105                 110

Asn Pro Ile Tyr Ala Asp Gly Ser His His His His His His
        115                 120                 125
```

<210> SEQ ID NO 3
<211> LENGTH: 116
<212> TYPE: PRT
<213> ORGANISM: Artificial
<220> FEATURE:
<223> OTHER INFORMATION: Lip with N123 glycosylation site of AcrA and
      hexa His tag

<400> SEQUENCE: 3

```
Met Lys Lys Thr Ala Ile Ala Ile Ala Val Ala Leu Ala Gly Phe Ala
1               5                   10                  15
```

```
Thr Val Ala Gln Ala Asp Val Ile Ile Lys Pro Gln Val Ser Gly Val
            20                  25                  30

Ile Val Asn Lys Leu Phe Lys Ala Gly Asp Lys Val Lys Lys Gly Gln
            35                  40                  45

Thr Leu Phe Ile Ile Glu Gln Asp Gln Asp Phe Asn Arg Ser Lys Ala
 50                  55                  60

Leu Asp His Thr Glu Ile Lys Ala Pro Phe Asp Gly Thr Ile Gly Asp
 65                  70                  75                  80

Ala Leu Val Asn Ile Gly Asp Tyr Val Ser Ala Ser Thr Thr Glu Leu
            85                  90                  95

Val Arg Val Thr Asn Leu Asn Pro Ile Tyr Ala Asp Gly Ser His His
            100                 105                 110

His His His His
        115

<210> SEQ ID NO 4
<211> LENGTH: 379
<212> TYPE: PRT
<213> ORGANISM: Artificial
<220> FEATURE:
<223> OTHER INFORMATION: AcrA protein with PelB signal sequence and hexa
      His tag

<400> SEQUENCE: 4

Met Lys Tyr Leu Leu Pro Thr Ala Ala Ala Gly Leu Leu Leu Leu Ala
 1               5                   10                  15

Ala Gln Pro Ala Met Ala Met His Met Ser Lys Glu Glu Ala Pro Lys
            20                  25                  30

Ile Gln Met Pro Pro Gln Pro Val Thr Thr Met Ser Ala Lys Ser Glu
            35                  40                  45

Asp Leu Pro Leu Ser Phe Thr Tyr Pro Ala Lys Leu Val Ser Asp Tyr
 50                  55                  60

Asp Val Ile Ile Lys Pro Gln Val Ser Gly Val Ile Val Asn Lys Leu
 65                  70                  75                  80

Phe Lys Ala Gly Asp Lys Val Lys Lys Gly Gln Thr Leu Phe Ile Ile
            85                  90                  95

Glu Gln Asp Lys Phe Lys Ala Ser Val Asp Ser Ala Tyr Gly Gln Ala
            100                 105                 110

Leu Met Ala Lys Ala Thr Phe Glu Asn Ala Ser Lys Asp Phe Asn Arg
            115                 120                 125

Ser Lys Ala Leu Phe Ser Lys Ser Ala Ile Ser Gln Lys Glu Tyr Asp
        130                 135                 140

Ser Ser Leu Ala Thr Phe Asn Asn Ser Lys Ala Ser Leu Ala Ser Ala
145                 150                 155                 160

Arg Ala Gln Leu Ala Asn Ala Arg Ile Asp Leu Asp His Thr Glu Ile
            165                 170                 175

Lys Ala Pro Phe Asp Gly Thr Ile Gly Asp Ala Leu Val Asn Ile Gly
            180                 185                 190

Asp Tyr Val Ser Ala Ser Thr Thr Glu Leu Val Arg Val Thr Asn Leu
            195                 200                 205

Asn Pro Ile Tyr Ala Asp Phe Phe Ile Ser Asp Thr Asp Lys Leu Asn
            210                 215                 220

Leu Val Arg Asn Thr Gln Ser Gly Lys Trp Asp Leu Asp Ser Ile His
225                 230                 235                 240

Ala Asn Leu Asn Leu Asn Gly Glu Thr Val Gln Gly Lys Leu Tyr Phe
            245                 250                 255
```

```
Ile Asp Ser Val Ile Asp Ala Asn Ser Gly Thr Val Lys Ala Lys Ala
            260                 265                 270

Val Phe Asp Asn Asn Ser Thr Leu Leu Pro Gly Ala Phe Ala Thr
            275                 280                 285

Ile Thr Ser Glu Gly Phe Ile Gln Lys Asn Gly Phe Lys Val Pro Gln
            290                 295                 300

Ile Gly Val Lys Gln Asp Gln Asn Asp Val Tyr Val Leu Leu Val Lys
305                 310                 315                 320

Asn Gly Lys Val Glu Lys Ser Ser Val His Ile Ser Tyr Gln Asn Asn
            325                 330                 335

Glu Tyr Ala Ile Ile Asp Lys Gly Leu Gln Asn Gly Asp Lys Ile Ile
            340                 345                 350

Leu Asp Asn Phe Lys Lys Ile Gln Val Gly Ser Glu Val Lys Glu Ile
            355                 360                 365

Gly Ala Gln Leu Glu His His His His His His
            370                 375
```

<210> SEQ ID NO 5
<211> LENGTH: 132
<212> TYPE: PRT
<213> ORGANISM: Artificial
<220> FEATURE:
<223> OTHER INFORMATION: CtxB protein with hexa His tag and OmpA signal
      sequence

<400> SEQUENCE: 5

```
Met Lys Lys Thr Ala Ile Ala Ile Ala Val Ala Leu Ala Gly Phe Ala
1               5                   10                  15

Thr Val Ala Gln Ala Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
            35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn Gly Ser His His
            115                 120                 125

His His His His
    130
```

<210> SEQ ID NO 6
<211> LENGTH: 290
<212> TYPE: PRT
<213> ORGANISM: Artificial
<220> FEATURE:
<223> OTHER INFORMATION: OmpH1 with myc tag

<400> SEQUENCE: 6

```
Met Lys Lys Ile Leu Leu Ser Val Leu Thr Thr Phe Val Ala Val Val
1               5                   10                  15

Leu Ala Ala Cys Gly Gly Asn Ser Asp Ser Lys Thr Leu Asn Ser Leu
            20                  25                  30

Asp Lys Ile Lys Gln Asn Gly Val Val Arg Ile Gly Val Phe Gly Asp
```

-continued

```
             35                  40                  45
Lys Pro Pro Phe Gly Tyr Val Asp Glu Lys Gly Asn Asn Gln Gly Tyr
    50                  55                  60

Asp Ile Ala Leu Ala Lys Arg Ile Ala Lys Glu Leu Phe Gly Asp Glu
65                  70                  75                  80

Asn Lys Val Gln Phe Val Leu Val Glu Ala Ala Asn Arg Val Glu Phe
                85                  90                  95

Leu Lys Ser Asn Lys Val Asp Ile Ile Leu Ala Asn Phe Thr Gln Thr
            100                 105                 110

Pro Glu Arg Ala Glu Gln Val Asp Phe Cys Leu Pro Tyr Met Lys Val
        115                 120                 125

Ala Leu Gly Val Ala Val Pro Lys Asp Ser Asn Ile Thr Ser Val Glu
    130                 135                 140

Asp Leu Lys Asp Lys Thr Leu Leu Leu Asn Lys Gly Thr Thr Ala Asp
145                 150                 155                 160

Ala Tyr Phe Thr Gln Asp Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Asp Val
            260                 265                 270

Val Ile Glu Gly Gly Lys Ile Leu Glu Gln Lys Leu Ile Ser Glu Glu
        275                 280                 285

Asp Leu
    290
```